(12) United States Patent
Aoki

(10) Patent No.: US 6,582,716 B2
(45) Date of Patent: Jun. 24, 2003

(54) METHOD FOR TREATING WOUNDS, PROMOTING HEALING AND AVOIDING AMPUTATIONS IN DIABETIC AND NON-DIABETIC PATIENTS

(76) Inventor: Thomas T. Aoki, 1021 El Sur Way, Sacramento, CA (US) 95825

( * ) Notice: Subject to any disclaimer, the term of this patent is extended or adjusted under 35 U.S.C. 154(b) by 43 days.

(21) Appl. No.: 09/881,835

(22) Filed: Jun. 15, 2001

(65) Prior Publication Data

US 2001/0053382 A1 Dec. 20, 2001

Related U.S. Application Data

(60) Provisional application No. 60/212,151, filed on Jun. 16, 2000.

(51) Int. Cl.[7] .................. A61K 38/28; A61K 31/70
(52) U.S. Cl. ................ 424/422; 424/423; 514/3; 514/4
(58) Field of Search ................. 424/422, 423, 424/400; 514/3, 4

(56) References Cited

U.S. PATENT DOCUMENTS 4,826,810 A 5/1989 Aoki

OTHER PUBLICATIONS

Furnary Ap, Zerr KJ, Grunkemeier GL, Starr A. Continuous intravenous insulin reduces the incidence of deep sternal wound infection in diabetic patients after cardiac surgical procedure. Annals of Thoracic Surgeon 1999; 67:352–362.*
Aoki, T. et al., "Chronic intermittent intravenous insulin therapy: a new frontier in diabetes therapy", Diabetes Technology and Therapeutics 2001 Spring; 3(1): 111–23.
Aoki Diabetes Research Institute, "CIIIT Treatment Results", Mar. 31, 2001.
Heinemann, "Pulsatile insulin infusion and glucose–homeostasis in well–controlled type 1 diebetic patients", Journal of Internal Medicine 1989, vol. 226, pp. 325–330.
Aoki, T. et al., "Long term intermittent intravenous insulin therapy and type 1 diabetes mellitus", The Lancet, vol. 342, Aug. 28, 1993, pp. 515–518.

* cited by examiner

Primary Examiner—Thurman K. Page
Assistant Examiner—Rachel M. Bennett
(74) Attorney, Agent, or Firm—Eric G. Masamori

(57) ABSTRACT

The present invention is a system and method capable of increasing glucose oxidation in an affected area and therefore providing more energy for treating wounds, promoting healing and avoiding amputations in both diabetic and non-diabetic patients. The current invention is the treating of wounds, promoting healing and avoiding lower extremity amputations using insulin pulses to a patient utilizing Chronic Intermittent Intravenous Insulin Therapy to achieve an increase in glucose oxidation in tissues surrounding an affected area, therefore treating wounds, promoting healing and avoiding amputations in both diabetic and non-diabetic patients.

6 Claims, No Drawings

METHOD FOR TREATING WOUNDS, PROMOTING HEALING AND AVOIDING AMPUTATIONS IN DIABETIC AND NON-DIABETIC PATIENTS

CROSS REFERENCE TO OTHER APPLICATIONS

This application claims the benefit of U.S. Provisional Patent Application No. 60/212,151 filed Jun. 16, 2000.

FIELD OF INVENTION

This invention relates to the treatment of wounds, promoting healing and avoiding amputations in diabetic and non-diabetic patients. More specifically, the invention relates to a system and method for treating wounds, promoting healing and avoiding amputations in diabetic and non-diabetic patients with Chronic Intermittent Intravenous Insulin Therapy.

BACKGROUND OF THE INVENTION

Diabetes is the number one cause of non-traumatic amputations. The common sources of amputations are wounds that will not heal and progress to necrosis and gangrene. It is generally observed that diabetic patients have greater difficulty in healing and in overcoming infections. Diabetes in general and poor blood glucose control in particular are thought to be causally related to poor wound repair in diabetic patients, is also a source of a lack of energy and a general feeling of malaise.

The first attempt to treat an ulcer in diabetic patients was to administer antibiotics, improve blood glucose control, and perform surgical debridement of the ulcer. The goal of this approach was to prevent septicemia, improve the metabolism of that patient by improving blood glucose control, decrease insulin resistance and removing necrotic material so that granulation could proceed. This approach has been mildly successful; however many of these patients go on to develop chronic non-healing ulcers which require intensive medical and surgical management.

What is needed is a system and method that increases glucose oxidation in the affected areas and therefore providing more energy while consuming less oxygen for treating wounds, promoting healing and avoiding lower extremity amputations in both diabetic and non-diabetic patients.

SUMMARY

Accordingly, the present invention is a system and method capable of increasing glucose oxidation in an affected area and therefore providing more energy and thereby providing more energy with the same oxygen delivery for treating wounds, promoting healing and avoiding amputations in both diabetic and non-diabetic patients. The current invention is the treating of wounds, promoting healing and avoiding amputations using insulin pulses to a patient utilizing Chronic Intermittent Intravenous Insulin Therapy to achieve an increase in glucose oxidation in tissue surrounding an affected area, therefore treating wounds, promoting healing and avoiding amputations in both diabetic and non-diabetic patients.

The rationale for this improved healing is that the tissue surrounding the affected area suffers from inadequate blood supply, leading to insufficient oxygenation. When this tissue is fueled through enhanced glucose oxidation in lieu of free fatty acid utilization, thereby switching from a predominantly lipid based fuel economy to one based more on glucose oxidation, more energy is available for wound healing for the same amount of blood flow and hence, more healing from the amount of oxygen delivered. In addition, the ability to achieve more energy from less oxygen, thereby addressing a general malaise associated with diabetic individuals who have energy levels which are less than normal.

One preferred embodiment of the invention is a system for treating wounds, promoting healing and avoiding amputations in diabetic and non-diabetic patients through an intravenous administration of a pulse of insulin comprises a means for determining a respiratory quotient of a patient, a liquid or food containing glucose, an intravenous site, and a means of delivering a pulse of insulin at a regular interval of time.

In the preferred embodiment of the treatment system, any instrument capable of measuring the respiratory quotient determines a respiratory quotient of a patient. The respiratory quotient is defined as the ratio of carbon dioxide produced to oxygen consumed by the patient. In the preferred embodiment, a liquid or food containing glucose is consumed by the patient to prevent hypoglycemia. The preferred liquid or food containing glucose is GLUCOLA, however any similar liquid or food containing glucose that will prevent hypoglycemia in the patient may be used.

The preferred means of delivering insulin is an infusion device. It is preferable that the infusion device is capable of providing pulses of insulin on a prearranged interval, so long as there is sufficient glucose in the blood to keep the patient from becoming hypoglycemic. The preferred infusion device is also capable of delivering the pulses of insulin in as short duration of time as possible, without adversely affecting the vein at the site of infusion is used. However, less accurate devices may deliver the pulses and achieve the needed infusion profile of approximately six minutes.

In the preferred embodiment, the intravenous site is a temporary or permanent IV access site located in the body, forearm or hand of the patient. The amount of insulin is tailored to achieve increased glucose utilization by the tissue surrounding the wound area. Increased glucose utilization is measured by a stabilization or decrease in 24 hour urinary protein excretion or stabilization or increase in creatinine clearance. Type 1 diabetic patients receive 20–35 milliunits of insulin per kilogram of body weight per pulse and type 2 diabetic patients receive 70–200 milliunits of insulin per kilogram of body weight per pulse. During periods of non-use, the IV site is preferably converted to a heparin or saline lock.

In one embodiment of the method of the invention, the patient is seated in a blood drawing chair and a 23 gauge needle/catheter is inserted into a hand or forearm vein to obtain vascular access. Although a 23 gauge needle catheter is preferred, any system of such access may accomplish the needed result, including indwelling catheters. After a short equilibration period, usually thirty minutes, the respiratory quotient (the ration of carbon dioxide produced to oxygen consumed by the patient) of the patient is measured. The respiratory quotient measuring device may be any presently known model manufactured by any presently known supplier of such instruments. In the preferred embodiment, the patient is then asked to drink or eat liquid or food containing glucose usually on the order of 60 to 100 grams of glucose. In the preferred embodiment a pulse of insulin is administered intravenously on a regular interval of time, usually every six minutes, until the respiratory quotient (RQ) shows improvement, as indicated by a respiratory quotient of 0.90 or greater. In the preferred embodiment, improvement in RQ is generally achieved within one hour. In the preferred embodiment, the insulin/oral glucose phase is then followed by a rest period of usually one hour. In the preferred embodiment the entire procedure repeated until the desired effect is achieved.

The preferred method of insulin pulse delivery would be a prearranged interval, so long as there is sufficient glucose in the blood to keep the patient from becoming hypoglycemic. In order to determine the progress of the patient, it is preferable the RQ is measured every hour and blood glucose levels are checked every 30 minutes. The blood glucose level may be measured by any means which shows that the patient is not becoming hypoglycemic. In the preferred embodiment, the patient is free to move around after the initial insulin pulses have been administered. In the preferred embodiment, the intravenous site is converted to a heparin or saline lock. The patient returns to the blood drawing chair to receive their next series of insulin pulses. In the preferred embodiment, the subsequent insulin pulses must be covered by supplying glucose by mouth or other means. The total time of the preferred procedure is approximately 6–7 hours.

In the preferred embodiment, two successive days of three treatments are performed with a new patient. In the preferred embodiment, the above is repeated once a week. For patients who need a more intensive approach, it is preferable the procedure be repeated 3 or more times, including continuously each week until the desired clinical outcome is achieved.

In the non-diabetic patient more glucose may be required than in the diabetic patient, but the other parameters would remain the same, including the need for a pulse delivery.

DETAILED DESCRIPTION OF THE INVENTION

The following description is provided to enable any person skilled in the art to use the invention and sets forth the best mode presently contemplated by the inventor of carrying out his invention. Various modifications, however, will remain readily apparent to those skilled in the art, as generic principles of the present invention have been defined herein.

The present invention is a system and method capable of increasing glucose oxidation in an affected area and therefore providing more energy for treating wounds, promoting healing and avoiding amputations in both diabetic and non-diabetic patients. The current invention is the treating of wounds, promoting healing and avoiding amputations using insulin pulses to a patient utilizing Chronic Intermittent Intravenous Insulin Therapy to achieve an increase in glucose oxidation in tissue surrounding an affected area, therefore treating wounds, promoting healing and avoiding amputations in both diabetic and non-diabetic patients.

The rationale for this improved healing is the tissue surrounding the affected area suffers from inadequate blood supply, leading to insufficient oxygenation. When this tissue is fueled through enhanced glucose oxidation in lieu of free fatty acid utilization, thereby switching from a predominantly lipid based fuel economy to one based more on glucose oxidation, more energy is available for wound healing for the same amount of blood flow and hence, more healing from the amount of oxygen delivered. In addition, the ability to achieve more energy from less oxygen, thereby addressing a general malaise associated with people who have energy levels which are less than normal.

Clinically, high glucose levels are usually associated with low glucose oxidation rates. Furthermore, high glucose levels (poor blood glucose control) are generally considered to interfere with wound healing. In an environment where conventional wisdom would suggest that high glucose levels interfere with wound healing, it is counter intuitive to seek to promote glucose utilization in the presence of elevated blood glucose levels.

The preferred embodiment of the invention is a system and method of delivering insulin pulses to a patient utilizing a Chronic Intermittent Intravenous Insulin Therapy. The preferred embodiment of the treatment system comprises a means for determining a respiratory quotient of a patient, a liquid or food containing glucose, an intravenous site, and a means of delivering a pulse of insulin at a regular interval of time.

The preferred means for determining a respiratory quotient of a patient is a SENSORMEDIC METABOLIC MEASUREMENT CART, however any instrument capable of measuring the respiratory quotient may be used. The respiratory quotient is defined as the ratio of carbon dioxide produced to oxygen consumed by the patient.

The liquid or food containing glucose is consumed by the patient to prevent the patient from becoming hypoglycemic. The preferred liquid or food containing glucose is GLUCOLA, but any similar type of liquid or food containing glucose may be given to the patient.

The preferred means of insulin delivery would be an infusion device capable of providing pulses of insulin on a prearranged interval, so long as there is sufficient glucose in the blood to keep the patient from becoming hypoglycemic. It is also preferable that the infusion device is capable of delivering the pulses of insulin in as short duration of time as possible, without adversely affecting the vein at the site of infusion is used. A BIONICA MD-110 infusion device is preferably used to administer the insulin pulses. However, less accurate devices may deliver the pulses and achieve the needed infusion profile of approximately six minutes.

In the preferred embodiment, the intravenous site is a temporary or permanent intravenous access site located in the body, forearm or hand of the patient, whereby insulin is provided by intravenous pulses in a highly accurate manner. A 23 gauge catheter has been used as the access site, however any type of similar temporary or permanent intravenous access may be used. The amount of insulin is tailored to achieve increased glucose utilization by the tissue surrounding the wound area. Increased glucose utilization is measured by a stabilization or decrease in 24 hour urinary protein excretion or stabilization or increase in creatinine clearance. Type 1 diabetic patients receive 20–35 milliunits of insulin per kilogram of body weight per pulse and type 2 diabetic patients receive 70–200 milliunits of insulin per kilogram of body weight per pulse. During periods of non-use, the intravenous site is preferably converted to a heparin or saline lock.

The preferred embodiment of the method of delivering insulin pulses to a patient utilizing Chronic Intermittent Intravenous Insulin Therapy is as follows. On the morning of the procedure, the patient is preferably seated in a blood drawing chair and a 23 gauge needle or catheter is preferably inserted into a hand or forearm vein to obtain vascular access. However, any system of such access may accomplish the needed result, including indwelling catheters PICC lines and PORTACATHs. After a short equilibration period the patient is asked to breathe into an instrument which measures the patient's respiratory quotient. Equilibrium is achieved when consecutive measurements of the respiratory quotient, at least 5 minutes apart, are the same. In practice the equilibration period was thirty minutes, however any period of time that allows patient to establish a steady baseline, may be used. It is preferable that a SENSOR-MEDIC METABOLIC MEASUREMENT CART be used to measure the respiratory quotient, however, any presently known model manufactured by any presently known supplier of instruments capable of measuring a respiratory quotient may be used.

After the RQ is obtained, the patient is asked to consume a liquid or food containing glucose. The amount of glucose given to the patient ranged from 60 to 100 grams, however the amount of initial glucose given to the patient may vary. A pulse of insulin is then administered intravenously on a regular interval of time until the measured RQ shows improvement, as indicated by a RQ of 0.90 or greater. In prototype testing the regular interval of time was every six minutes, however, other regular intervals of time may be used. Improvement in RQ is generally achieved within one hour, however, the time required for RQ improvement may be shorter or longer than one hour.

The insulin/glucose phase is followed by a rest period of usually one hour. The rest period allows the elevated insulin levels to return to baseline. The entire procedure is repeated until the desired effect, RQ greater than 0.90, is achieved. The preferred method of insulin delivery would be providing pulses of insulin on a prearranged interval, so long as there is sufficient glucose in the blood to keep the patient from becoming hypoglycemic. In order to determine the progress of the patient, the RQ is measured every hour and blood glucose levels are checked every thirty minutes by any means which shows that the patient is not becoming hypoglycemic.

Once the insulin pulses have been administered and the patient shows RQ improvement as indicated by a RQ of 0.90 or greater, the patient is provided a rest period. During the rest period the patient is allowed to move around until the next series of insulin pulses are administered. During the rest period the IV site is preferably converted to a heparin or saline lock. The total time of the procedure is approximately 6–7 hours.

The amount of insulin is tailored to achieve increased glucose utilization by the tissue surrounding the wound area. Type 1 diabetic patients receive 20–35 milliunits of insulin per kilogram of body weight per pulse and type 2 diabetic patients receive 70–200 milliunits of insulin per kilogram of body weight per pulse.

Usually with a new patient two successive days of three treatments are performed the first week. For continuing patients the procedure is performed once a week For patients who need/require a more intensive approach, the procedure may be repeated 3 or more times, including continuously, each week until the desired clinical outcome is achieved. The desired clinical outcomes are improved wound healing and decrease in wound size. The more intensive approach is designed for patients who show insufficient progress with respect to wound healing or wound size.

In the non-diabetic patient more glucose may be required than in the diabetic patient, but the other parameters would remain the same, including the need for pulse delivery.

The effect of Chronic Intermittent Intravenous Insulin Therapy (CIIIT) is to increase glucose oxidation by tissues surrounding the wound and decrease free fatty acid levels by inhibiting lipolysis (the lower free fatty acid levels in turn, de-inhibit the pyruvate dehydrogenase complex.) In addition, the high insulin pulses directly stimulate and activate the pyruvate dehydrogenase complex, thereby increasing glucose oxidation and generating ATP for wound healing. The result is to allow the patient to produce more ATP for the same amount of oxygen available. A further result is the reversal of a malaise associated with a lack of sufficient energy.

The preferred embodiments described herein are illustrative only, and although the examples given include many specificity's, they are intended as illustrative of only a few possible embodiments of the invention. Other embodiments and modifications will, no doubt, occur to those skilled in the art. The examples given should only be interpreted as illustrations of some of the preferred embodiments of the invention, and the full scope of the invention should be determined by the appended claims and their legal equivalents.

What is claimed is:

1. A method for treating wounds, promoting healing and avoiding amputations in diabetic and non-diabetic patients by improving the dietary fuel capabilities and correct an overutilization of free fatty acids thereby enhancing available energy in tissue surrounding an affected area comprising the steps of:

a) determining a steady baseline respiratory quotient of a patient and obtaining a subsequent respiratory quotient every 30 minutes, the steady baseline respiratory quotient being two identical consecutive respiratory quotients less than 0.90 measured five minutes apart, b) having the patient consume a liquid or food containing 60 to 100 grams of glucose, c) administering a pulse of insulin through an intravenous site at a six minute interval of time until the subsequent respiratory quotient shows an improvement over the steady baseline respiratory quotient, the pulse of insulin being 20 to 35 milliunits of insulin per kilogram of body weight for a non-diabetic and a Type I diabetic, the pulse of insulin being 70–200 milliunits of insulin per kilogram of body weight for a Type II diabetic, the improvement over the steady baseline respiratory quotient being a respiratory quotient of 0.90 or greater, the subsequent respiratory quotient improvement over the steady baseline respiratory quotient being a measurement of increased glucose oxidation by tissue surrounding the affected area;

d) allowing the patient to rest one hour, and e) repeating the steps a–d at least three times.

2. The method of claim 1, wherein the intravenous site further comprises a needle or catheter located in the patient's body, hand or forearm.

3. The method of claim 1, wherein the pulse of insulin is administered by an intravenous infusion device.

4. The method of claim 1, wherein the intravenous site is converted to a heparin or a saline lock during step (d).

5. The method of claim 1, wherein said steps a–e are repeated at least once a week.

6. The method of claim 5, wherein said steps a–e are repeated three or more times a week.

* * * * *